(12) United States Patent
Yoshimatu

(10) Patent No.: US 6,391,269 B1
(45) Date of Patent: May 21, 2002

(54) DEODORIZING/STERILIZING DEVICE

(75) Inventor: Takeshiro Yoshimatu, Tokyo (JP)

(73) Assignees: Takeshiro Yoshimatsu, Tokyo; Kenji Nakamura, Osaka, both of (JP)

( * ) Notice: Subject to any disclaimer, the term of this patent is extended or adjusted under 35 U.S.C. 154(b) by 0 days.

(21) Appl. No.: 09/486,058

(22) PCT Filed: Aug. 4, 1998

(86) PCT No.: PCT/JP98/03456

§ 371 Date: May 25, 2000

§ 102(e) Date: May 25, 2000

(87) PCT Pub. No.: WO99/10273

PCT Pub. Date: Mar. 4, 1999

(30) Foreign Application Priority Data

Aug. 21, 1997 (JP) .............................................. 9-240317

(51) Int. Cl.[7] .................................................. B01J 19/08
(52) U.S. Cl. .................................................. 422/186.07
(58) Field of Search ................................... 422/186.07

(56) References Cited

U.S. PATENT DOCUMENTS 6,042,699 A * 3/2000 Cribbin et al. ......... 422/186.04

FOREIGN PATENT DOCUMENTS

| JP | 50-1008 | 1/1975 |
|---|---|---|
| JP | 63-40705 | 2/1988 |
| JP | 4-110725 | 9/1992 |

* cited by examiner

*Primary Examiner*—Kathryn Gorgos
*Assistant Examiner*—Thao Tran
(74) *Attorney, Agent, or Firm*—Knobbe, Martens, Olson and Bear, LLP.

(57) ABSTRACT

A deodorizing/sterilizing device having a cylindrical electrode formed of a sintered metal which mainly contains titanium oxide and can be easily machined by rolling and cutting and a needle-like electrode located generally on the center axis of the cylindrical electrode. By applying a current of high frequency and high voltage, ultraviolet radiation is emitted from the needle-like electrode. The electrode material is little corroded by ozone. Air flows along the inner peripheral surface of the cylindrical electrode, ultraviolet radiation is emitted from the needle-like electrode, the cylindrical electrode has the function of an optical catalyst to achieve deodorization and sterilization.

6 Claims, 2 Drawing Sheets

Voltage kV

Frequency kHz

DEODORIZING/STERILIZING DEVICE

FIELD OF THE INVENTION

This invention relates to an ozone generator, and more particularly, to a deodorizing and sterilizing apparatus including the ozone generator, the electrode of which has the photo-catalytic function, the high corrosion resistance against ozone and the high mechanical workability.

This invention also relates to a photo-catalytic material, and more particularly, a photo-catalytic electrode used in the ozone generator and a method for manufacturing the photo-catalytic material.

BACKGROUND OF THE INVENTION

The conventional ion and/or ozone generator of a compact and easy-to-handle type is not guaranteed for generating ozone. The electrode of such an ozone generator is easily oxidized due to a strong oxidative property of ozone and can not have a long-durability by the corrosion due to ozone. Accordingly, the conventional ions and ozone generators have only an insufficient deodorizing and sterilizing effect.

Therefore, it is an object of the invention to provide a photo-catalytic electrode material with a high corrosional resistance against ozone.

It is another object of the invention to provide a deodorizing and sterilizing device of a compact, easy-to-handle and less expensive type which makes the electrode emit ultra-violet rays to activate the photo-catalytic function of the electrode.

SUMMARY OF THE INVENTION

An ion/ozone generator according to the invention includes a cylindrical electrode and a needle-like electrode, which are made of titanium oxide, the tip of which is positioned on substantially the center axis of the cylindrical electrode and emits ultra-violet radiation. The ion/ozone generator has an air flow along the inner surface of the cylindrical electrode.

In another aspect of the invention, as a cylindrical electrode is made of a photo-catalytic material and a tip of a needle-like electrode emits ultra-violet rays, the ion/ozone generator of the invention has a photo-catalytic function.

In yet another aspect of the invention, the tip of the needle-like electrode is positioned substantially on the center axis of the cylindrical electrode and with an interval from the end of the cylindrical electrode.

The electrode used in the ion/ozone generator of the invention is formed of the photo-catalytic material made of the sintered and rolled titanium oxide. In another aspect, the electrode is formed of the plate-like material made of the sintered and rolled titanium oxide powder to which a slight amount of iron, carbon, nickel and/or zirconium are added for improving the mechanical workability of the sintered titanium oxide.

In still another aspect of the invention, a method for producing a photo-catalytic material used for electrodes is provided. In this method, powder of titanium oxide, in which a slight amount of iron, carbon, copper, nickel, and/or zirconium is added in order to improve the property of a sintered metal, is heated and melted at a temperature lower than the melting point in the atmosphere. Then, a plate-like ingot is formed. The ingot is rolled out repeatedly in order to form a plate with a predetermined thickness, which is easy to machine, bend, and cut. Finally, the ingot plate is cut into multiple pieces having predetermined sizes, which are then shaped into cylindrical electrodes or needle-like electrodes.

If a full-wave rectified high-frequency and high-voltage direct current is applied between a needle-like electrode and a cylindrical electrode, the needle-like electrode discharges and produces a beam containing ultra-violet rays. In accordance with the invention, this phenomenon was recognized in the extent of the so-called silent discharge. The ozone and ions flow along the inner surface of the cylindrical electrode. The ultra-violet rays emitted from the tip of the needle electrode activate the photo-catalytic function of the cylindrical electrode. Since the cylindrical electrode is made of a material containing titanium oxide, it has a photo-catalytic function, which is stimulated by ultra-violet rays. An air current containing the stream of ions and ozone flows along the inner surface of the cylindrical electrode, while it is being subjected to both the photo-catalytic action due to the ultra-violet rays and oxidation due to ozone. Consequently, odor components contained in the air current are rapidly decomposed and deodorized by the oxidation ability of ozone. At the same time, bacteria contained in the air current are also sterilized.

Figure 1:
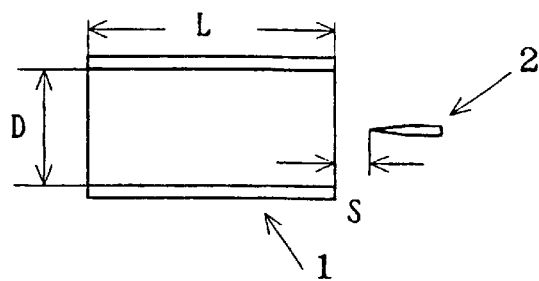
FIG. 1 illustrates a cylindrical electrode 1 and a needle electrode 2 in a cross-sectional view according to an embodiment of the invention. "D" denotes the inner diameter of the cylindrical electrode 1, "L" denotes the length of the cylindrical electrode 1, and "S" denotes the distance between the end of the cylindrical electrode 1 and the tip of the needle electrode 2.
Figure 2:
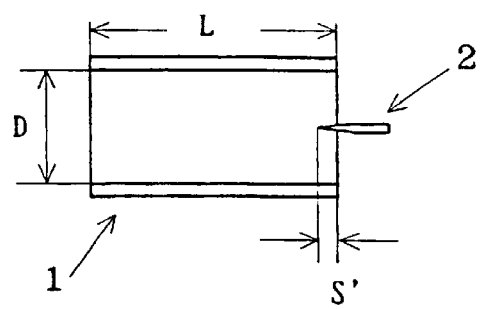
FIG. 2 illustrates a cylindrical electrode 1 and a needle electrode 2 in a cross-sectional view according to another embodiment of the invention, in which the tip of the needle electrode is placed in the cylindrical electrode 1 at one end of the cylindrical electrode.

By setting the distance "S " shown in FIG. 1 approximately, for example, to 2.5 mm, the velocity of the ion stream increases, as compared with the arrangement shown in FIG. 2, in which the tip of the needle electrode 2 is inserted in the cylindrical electrode 1. This also applies to the case in which S', which is the length of the insertion of the tip of the needle electrode 2 from the end of the cylindrical electrode 2, is zero.

Figure 3:
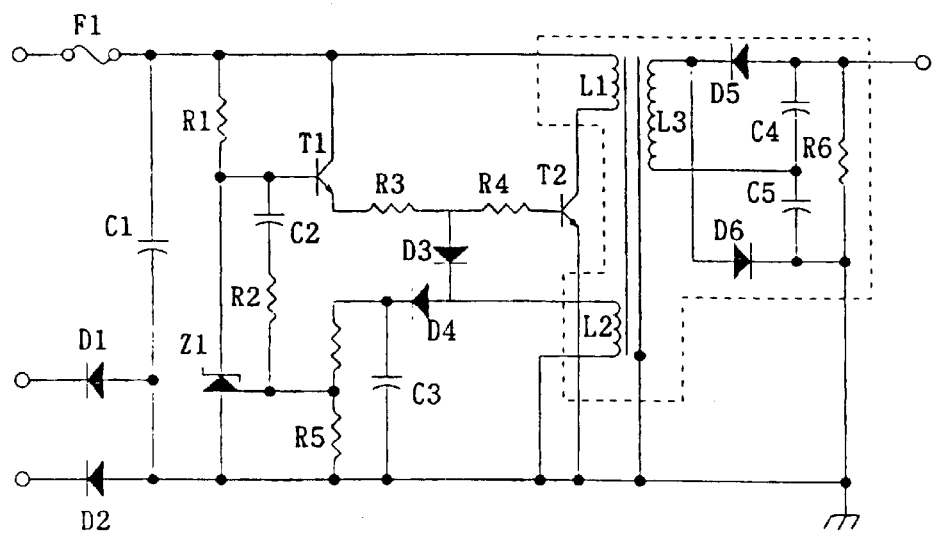

FIG. 3 illustrates an example of a circuit for producing a high-frequency and high-voltage direct current using a 100-volt commercial power source as a direct-current power supply.

Figure 4:
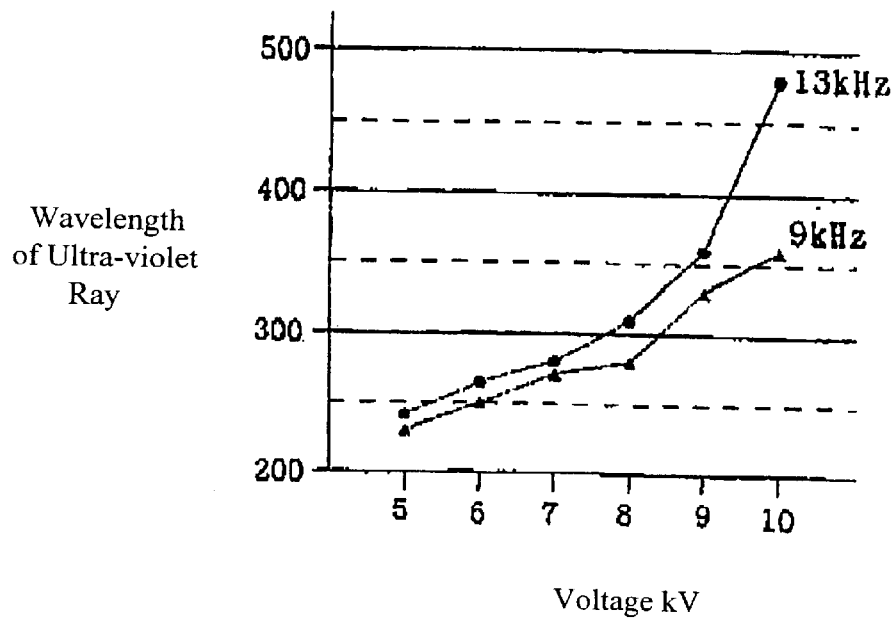

FIG. 4 shows the relationships between the wave-length of the ultra-violet rays produced by the needle electrode and the applied voltage at different frequencies.

Figure 5:
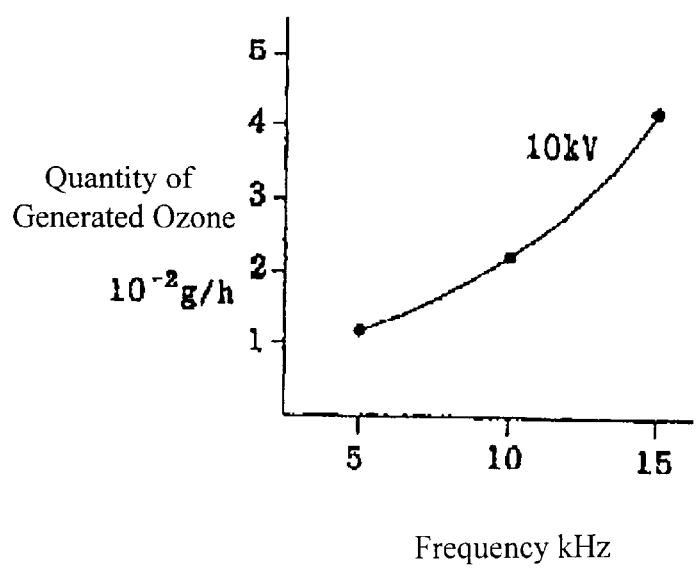

FIG. 5 is a graph of the amount of generated ozone vs. frequency of the direct current applied to the needle electrode at a certain voltage of the direct-current power supply.

PREFERRED EMBODIMENT OF THE INVENTION

In the process of manufacturing the electrode, powder of titanium oxide, to which a slight amount of iron, carbon, copper, nickel, and/or zirconium is added in order to improve the property of the sintered titanium oxide, is heated and melted at a temperature lower than the melting point in the atmosphere. Then, a plate-like ingot is formed. The plate-like ingot is rolled out repeatedly several times to become a plate with a predetermined thickness. This plate keeps the favorable property and ability of titanium oxide and becomes able to have the favorable mechanical workability during the sintering process of the invention. The plate is divided into multiple plate-like pieces with predetermined dimensions by cutting. A cylindrical electrode is formed of the plate-like piece by bending and welding. A needle-like electrode is formed of the plate-like piece by cutting and machining. According to the method for sintering titanium oxide of the invention, the sintered titanium oxide material keeps the favorable property and ability of itself and gets the favorable mechanical workability.

To be more precise, 0.07% to 0.1% iron, 0.03% carbon, 0.6% nickel, and 0.5% zirconium are mixed into powder of titanium oxide. Alternatively, 0.05% iron, 0.02% carbon, 0.4% nickel, and 1.0% zirconium are mixed into titanium oxide powder. The mixed titanium oxide powder is heated and melted at 1180° C. to 1300° C. in the atmosphere. The melted titanium oxide is shaped into a plate ingot having a thickness of 10 mm. The plate ingot is rolled out several times up to an appropriate thickness, for example, 0.05 mm. This rolling process decreases the number of air sacs inside the plate of titanium oxide, and allows the ingot to be dense and uniform. During the rolling process, the mechanical workability is improved and the favorable corrosion resistance against ozone is maintained.

Then, the plate is out into small pieces with an appropriate size. The piece is bent into a cylindrical shell, and the connection edges are welded, whereby a cylindrical electrode is completed. A needle-like electrode is formed by cutting a strip out of the plate, and by sharpening the strip into a needle-like bar.

If an electrode material is made of the sintered non-mixed titanium oxide powder, such material will be too fragile or hard to be mechanically worked, cut or bent. Cutting it produces hot saw-toothed swarf and scatters them, which may cause fire. It is as difficult as pure titanium material to be cut. Beside, such sintered titanium oxide material is too fragile or hard to be rolled, machined, cut and bent into cylindrical shapes.

But cutting the titanium oxide material sintered and rolled by way of this invention produces continued swarf, which allows the sintered material made of titanium oxide to be cut easily. Adding a slight amount of zirconium allows it to be bent, for example, cylindrically. In these embodiments, rutile type titanium oxide is used. However other type of titanium oxide can be used as well as rutile type.

In order to generate ultra-violet rays from the tip of the needle electrode, a high-frequency and high-voltage direct current must be applied between the needle electrode and the cylindrical electrode. In experiment, the needle electrode was always kept negative, and direct current was generated at frequencies of 9 kHz and 13 kHz with a voltage varied in the range of 5 to 10 kV. The wavelength of the violet rays generated from the tip of the needle electrode changes as the frequency and the voltage were varied. In the selected range of the voltage and at the selected frequencies, the wavelength of the generated ultra-violet rays was 230 nm to 480 nm, as shown in FIG. 3 (Should be FIG. 4). The amount of ozone generated during the discharge is shown in FIG. 4 (Should be FIG. 5).

In experiment, the inner diameter D and the length L of the cylindrical electrode was set to 19 mm and 20 mm, respectively, and the distance S between the tip of the needle electrode and the closer end of the cylindrical electrode was set to 2.5 mm. By keeping the needle electrode negative, a direct current of 9 kHz to 13 kHz was applied between the needle electrode and the cylindrical electrode with the voltage varied in the range of 5 kV to 10 kV. Corona discharge occurred, and the needle electrode started generating beams containing ultra-violet rays.

This phenomenon was recognized in a part of the silent discharge, where ions and ozone were generated. The minus-ions generated in the tip of the needle-like electrode flow toward the end part of the cylindrical electrode charged with plus. This ion flow entrains the air including ions/ozone around the flow and then flows along the inner surface of the cylindrical electrode.

The ultra-violet rays activate the photo-catalytic function of the cylindrical electrode made of sintered titanium oxide material. The air flow along the inner surface of the cylindrical electrode, which works as a photo-catalyst by the ultra-violet rays, is therefor acted by the photo-catalytic function and is also oxidized by ozone contained in the air itself. The odor components contained in the air current were rapidly decomposed and deodorized by the catalytic function of the titanium oxide and oxidation due to ozone. Bacteria contained in the air current were also sterilized. Ions and ozone are favorably produced in the part of the silent discharge conditioned by the present invention. At the same time, the ultra-violet rays emitted from the tip of the needle electrode activate the photo-catalytic function of the cylindrical electrode. Consequently, an air current flowing along the inner face of the cylindrical electrode is subjected to a highly efficient oxidation action.

INDUSTRIAL UTILIZATION

By applying a high-frequency and a high-voltage direct current between the electrodes made of titanium oxide material and emitting ultra-violet rays from the tip of the needle-like electrode, the deodorizing and sterilizing apparatus of the present invention can be fabricated a simple and compact structure and can deodorize and sterilize the air very efficiently. Since the electrodes are hardly corroded or oxidized by ozone and ion, the photo-catalytic function can be performed efficiently, therefore, odor components contained in the air flow along the inner surface of the cylindrical electrode can be decomposed rapidly into non-odor components, and at the same time bacteria in the air can be oxidized and sterilized.

What is claimed is:

1. An ion/ozone generator comprising:
   a cylindrical electrode, as a positive electrode, for generating ozone by photo-catalytic reaction, said cylindrical electrode being made of a rolled titanium oxide alloy; and
   a needle-shaped electrode, as a negative electrode, for emitting ultra-violet rays toward the cylindrical electrode when a high-frequency and high-voltage direct current is applied between the needle-shaped electrode and the cylindrical electrode, said needle-shaped electrode being made of a rolled titanium oxide alloy and aligned substantially with a center axis of the cylindrical electrode, the needle-shaped electrode having a body and a point, said point being positioned at an opening of the cylindrical electrode, said body being positioned outside the cylindrical electrode.

2. The ion/ozone generator according to claim 1, wherein the rolled titanium oxide alloy comprises at least one additive selected from the group consisting of iron, carbon, nickel, and zirconium in an amount effective to improve the machinability of sintered titanium oxide.

3. The ion/ozone generator according to claim 2, wherein the rolled titanium oxide alloy comprises 0.05–0.1% by weight of iron, 0.02–0.03% by weight of carbon, 0.4–0.6% by weight of nickel, and 0.5–1.0% by weight of zirconium.

4. The ion/ozone generator according to claim 1, wherein the point of the needle-shaped electrode is outside the cylindrical electrode, and the distance between the point of the cylindrical electrode and a plane defined by the opening of the cylindrical electrode is approximately 2.5 mm.

5. The ion/ozone generator according to claim 1, further comprising a power supply for applying a high-frequency and high-voltage direct current between the needle-shaped electrode and the cylindrical electrode.

6. The ion/ozone generator according to claim 5, wherein the power supply apples a current having a frequency of 9–13 kHz and a voltage of 5–10 kV.

* * * * *